US012714687B2

(12) United States Patent
Vidyasagar et al.

(10) Patent No.: US 12,714,687 B2
(45) Date of Patent: Aug. 25, 2026

(54) FORMULATIONS AND METHODS FOR TREATING DIARRHEA

(71) Applicants: UNIVERSITY OF FLORIDA RESEARCH FOUNDATION, INC., Gainesville, FL (US); AMILYFE, LLC, Norwood, MA (US)

(72) Inventors: Sadasivan Vidyasagar, Gainesville, FL (US); Astrid Grosche, Gainesville, FL (US); Xiaodong Xu, Gainesville, FL (US); Shanshan Lin, Gainesville, FL (US); Stephen Gatto, Norwood, MA (US); Robert Kenefick, Norwood, MA (US); Samuel Cheuvront, Norwood, MA (US)

( * ) Notice: Subject to any disclaimer, the term of this patent is extended or adjusted under 35 U.S.C. 154(b) by 770 days.

(21) Appl. No.: 18/000,541

(22) PCT Filed: Jun. 2, 2021

(86) PCT No.: PCT/US2021/035376
§ 371 (c)(1),
(2) Date: Dec. 2, 2022

(87) PCT Pub. No.: WO2021/247652
PCT Pub. Date: Dec. 9, 2021

(65) Prior Publication Data

US 2023/0210798 A1 Jul. 6, 2023

Related U.S. Application Data

(60) Provisional application No. 63/033,697, filed on Jun. 2, 2020.

(51) Int. Cl.
*A61K 31/198* (2006.01)
*A61K 31/401* (2006.01)
(Continued)

(52) U.S. Cl.
CPC .......... *A61K 31/198* (2013.01); *A61K 31/401* (2013.01); *A61K 31/7004* (2013.01); *A61K 31/7016* (2013.01); *A61P 1/12* (2018.01)

(58) Field of Classification Search
CPC .............. A61K 2300/00; A61K 31/198; A61K 31/401; A61K 31/7004; A61K 31/7016; A61K 35/74; A61P 1/12; Y02A 50/30
See application file for complete search history.

(56) References Cited

U.S. PATENT DOCUMENTS

2004/0067224 A1 4/2004 Ernest
2012/0077748 A1 3/2012 Vidyasagar et al.
(Continued)

FOREIGN PATENT DOCUMENTS

CN 102552250 A 7/2012
JP 58-088323 A 5/1983
(Continued)

OTHER PUBLICATIONS

International Search Report to corresponding International Application No. PCT/US2021/035376 mailed Sep. 9, 2021 (2 pages).
(Continued)

*Primary Examiner* — Savitha M Rao
(74) *Attorney, Agent, or Firm* — Dennemeyer & Associates LLC

(57) ABSTRACT

Amino acid formulations useful for treating diarrhea in a subject in need thereof are described herein. Such amino acid formulations and methods comprising administering same to a subject are useful for treating diarrhea, particularly diarrhea caused by or associated with bacterial infections wherein secretagogue-stimulated anion secretion from the intestinal crypt contributes to at least one symptom of diarrhea in the subject. Use of these amino acid formulations for the treatment of diarrhea in general or diarrhea associated with secretagogue-stimulated anion secretion from the intestinal crypt are encompassed herein, as are their use in the preparation of a medicament for the treatment of diarrhea in general or diarrhea associated with secretagogue-stimulated anion secretion from the intestinal crypt.

20 Claims, 3 Drawing Sheets

(51) Int. Cl.
*A61K 31/7004* (2006.01)
*A61K 31/7016* (2006.01)
*A61P 1/12* (2006.01)

(56) References Cited

U.S. PATENT DOCUMENTS

| | | | |
|---|---|---|---|
| 2014/0315800 | A1 | 10/2014 | Ochiai et al. |
| 2014/0377374 | A1 | 12/2014 | Vidyasagar et al. |

FOREIGN PATENT DOCUMENTS

| | | | |
|---|---|---|---|
| JP | 2003-530411 | A | 10/2003 |
| JP | 2006-511504 | A | 4/2006 |
| JP | 2015-506981 | A | 3/2015 |
| WO | 2010090423 | A2 | 8/2010 |
| WO | 2019070753 | A1 | 4/2019 |

OTHER PUBLICATIONS

Balakrishna Vuyyala, *Tamarindus indica* L. (Fabaceae): Extent of Explored Use in Traditional Medicine, Asian Journal of Pharmaceutical and Clinical Research.

Zeljan Males, Investigation of the composition of amino acids in Christ's thorn, 2001, 57(7), pp. 257-265.

FORMULATIONS AND METHODS FOR TREATING DIARRHEA

RELATED APPLICATIONS

This application is a U.S. National Phase application under 35 U.S.C. § 371 of International Application Number PCT/US2021/035376, filed Jun. 2, 2021, which claims priority to U.S. Provisional Application No. 63/033,697 filed Jun. 2, 2020, the entirety of each of which is incorporated herein by reference for all purposes.

FIELD OF THE INVENTION

Amino acid formulations useful for treating diarrhea in a subject in need thereof are described herein. Amino acid formulations and methods described herein are useful for treating diarrhea, particularly diarrhea caused by or associated with bacterial infections wherein secretagogue-stimulated anion secretion from the intestinal crypt contributes to at least one diarrheal symptom in such subjects. Use of these amino acid formulations for the treatment of diarrhea in general or diarrhea associated with secretagogue-stimulated anion secretion from the intestinal crypt and in the preparation of a medicament for the treatment of diarrhea in general or diarrhea associated with secretagogue-stimulated anion secretion from the intestinal crypt are also encompassed herein.

BACKGROUND OF THE INVENTION

Secretory diarrhea remains a substantial cause of mortality and morbidity worldwide, particularly in vulnerable populations such as children and the elderly. Indeed, infectious diarrhea is a leading cause of child mortality, resulting in fatal dehydration due to loss of electrolytes and water, and intestinal inflammation. After introducing sugar-based World Health Organization Oral Rehydration Solution (WHO-ORS) in 1979, mortality due to infectious diarrhea decreased significantly in children. Nevertheless, nearly 446,000 children still die every year due to infectious diarrhea. Children aged <5 years and adults aged >70 years are particularly at risk for mortality due to diarrheal diseases.

SUMMARY

Covered embodiments are defined by the claims, not this summary. This summary is a high-level overview of various aspects and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

In some embodiments, a formulation for use in treating diarrhea in a subject in need thereof is presented, wherein the formulation comprises a therapeutically effective combination of free amino acids: the free amino acids consisting essentially of or consisting of a therapeutically effective amount of free amino acids of proline and aspartic acid; and a therapeutically effective amount of at least one of free amino acids of serine, threonine, glycine, alanine, arginine, or tyrosine, or any combination thereof; and optionally, free amino acids of asparagine; or optionally, monosaccharide glucose, at least one glucose-containing disaccharide, or any combination thereof, wherein the total concentration of the monosaccharide glucose, the at least one glucose-containing disaccharide, or any combination thereof is equal to or less than 90 mM; or optionally, at least one pharmaceutically acceptable carrier, buffer, electrolyte, adjuvant, excipient, or water, or any combination thereof; or any combination thereof; and wherein the therapeutically effective combination of free amino acids is sufficient to reduce at least one symptom associated with the diarrhea in the subject.

In some embodiments of the formulation, the concentration of proline ranges from 0.5 mM to 13 mM; wherein the concentration of proline ranges from 0.8 mM to 13 mM; wherein the concentration of proline ranges from 2 mM to 10 mM; wherein the concentration of proline ranges from 6 mM to 10 mM; wherein the concentration of proline ranges from 8 mM to 10 mM; wherein the concentration of proline ranges from 8.1 mM to 9.9 mM; or wherein the concentration of proline is 9 mM.

In some embodiments of the formulation, the concentration of aspartic acid ranges from 1 mM to 18 mM; wherein the concentration of aspartic acid ranges from 1 mM to 12 mM; wherein the concentration of aspartic acid ranges from 8 mM to 12 mM; wherein the concentration of aspartic acid ranges from 9 mM to 11 mM; or wherein the concentration of aspartic acid is 10 mM.

In some embodiments of the formulation, when serine is present, the concentration of serine ranges from 1.5 mM to 12 mM; wherein the concentration of serine ranges from 4 mM to 10 mM; wherein the concentration of serine ranges from 8 mM to 12 mM; wherein the concentration of serine ranges from 9 mM to 11 mM or wherein the concentration of serine is 10 mM.

In some embodiments of the formulation, when threonine is present, the concentration of threonine ranges from 0.5 mM to 12 mM; the concentration of threonine ranges from 2 mM to 12 mM; wherein the concentration of threonine ranges from 4 mM to 10 mM; wherein the concentration of threonine ranges from 6 mM to 10 mM; wherein the concentration of threonine ranges from 7.2 mM to 8.8 mM; or wherein the concentration of threonine is 8 mM.

In some embodiments of the formulation, when glycine is present, the concentration of glycine ranges from 0.4 mM to 12 mM; wherein the concentration of glycine ranges from 1 mM to 10 mM; wherein the concentration of glycine ranges from 5 mM to 8 mM; wherein the concentration of glycine ranges from 6 mM to 8 mM; wherein the concentration of glycine ranges from 6.3 mM to 7.8 mM; or wherein the concentration of glycine is 7 mM.

In some embodiments of the formulation, when alanine is present, the concentration of alanine ranges from 1.5 mM to 12 mM; wherein the concentration of alanine ranges from 3 mM to 9 mM; wherein the concentration of alanine ranges from 4 mM to 7 mM; wherein the concentration of alanine ranges from 4 mM to 6 mM; wherein the concentration of alanine ranges from 4.8 mM to 5.8 mM; or wherein the concentration of alanine is 5.3 mM.

In some embodiments of the formulation, when arginine is present, the concentration of arginine ranges from 0.8 mM to 12 mM; wherein the concentration of arginine ranges from 5 mM to 10 mM; wherein the concentration of arginine ranges from 5 mM to 8 mM; wherein the concentration of arginine ranges from 6 mM to 8 mM; wherein the concentration of arginine ranges from 6 mM to 7.4 mM; or wherein the concentration of arginine is 6.7 mM.

In some embodiments of the formulation, when tyrosine is present, the concentration of tyrosine ranges from 0.1 mM to 1.2 mM; the concentration of tyrosine ranges from 0.5 mM to 1.2 mM; wherein the concentration of tyrosine ranges from 0.8 mM to 1.2 mM; wherein the concentration of tyrosine ranges from 0.9 mM to 1.2 mM; wherein the concentration of tyrosine ranges from 1.0 mM to 1.3 mM; or wherein the concentration of tyrosine is 1.2 mM.

In some embodiments of the formulation, when asparagine is present, the concentration of asparagine ranges from 2 mM to 12 mM; wherein the concentration of asparagine ranges from 2 mM to 10 mM; or wherein the concentration of asparagine ranges from 6 mM to 8 mM; or wherein the concentration of asparagine ranges from 6.9 mM to 8.5 mM; wherein the concentration of asparagine is 7.7 mM.

In some embodiments of the formulation, the therapeutically effective combination of free amino acids consists essentially of or consists of a therapeutically effective amount of free amino acids of proline, aspartic acid, serine, threonine, glycine, alanine, arginine, and tyrosine.

In some embodiments of the formulation, the therapeutically effective combination of free amino acids consists essentially of or consists of a therapeutically effective amount of free amino acids of proline, aspartic acid, serine, threonine, glycine, alanine, arginine, and tyrosine, wherein the concentration of proline is 8-10 mM; wherein the concentration of aspartic acid is 9-11 mM; wherein the concentration of serine is 9-11 mM; wherein the concentration of threonine is 7-9 mM; wherein the concentration of glycine is 6-8 mM; wherein the concentration of alanine is 5-6 mM; wherein the concentration of arginine is 6-7 mM; and wherein the concentration of tyrosine is 0.8-1.2 mM.

In some embodiments of the formulation, the therapeutically effective combination of free amino acids consists essentially of or consists of a therapeutically effective amount of free amino acids of proline, aspartic acid, serine, threonine, glycine, alanine, arginine, and tyrosine, wherein the concentration of proline is 9 mM; wherein the concentration of aspartic acid is 10 mM; wherein the concentration of serine is 10 mM; wherein the concentration of threonine is 8 mM; wherein the concentration of glycine is 7 mM; wherein the concentration of alanine is 5.3 mM; wherein the concentration of arginine is 6.7 mM; and wherein the concentration of tyrosine is 1.2 mM.

In some embodiments of the formulation, the therapeutically effective combination of free amino acids consists essentially of or consists of a therapeutically effective amount of free amino acids of proline, aspartic acid, serine, threonine, glycine, alanine, arginine, and tyrosine, wherein the concentration of proline is 9-11 mM; wherein the concentration of aspartic acid is 15-17 mM; wherein the concentration of serine is 7-9 mM; wherein the concentration of threonine is 3-5 mM; wherein the concentration of glycine is 5-7 mM; wherein the concentration of alanine is 5-7 mM; wherein the concentration of arginine is 5-7 mM; and wherein the concentration of tyrosine is 0.8-1.2 mM.

In some embodiments of the formulation, the therapeutically effective combination of free amino acids consists essentially of or consists of a therapeutically effective amount of free amino acids of proline, aspartic acid, serine, threonine, glycine, alanine, arginine, and tyrosine, wherein the concentration of proline is 10 mM; wherein the concentration of aspartic acid is 15.9 mM; wherein the concentration of serine is 8 mM; wherein the concentration of threonine is 4.3 mM; wherein the concentration of glycine is 5.7 mM; wherein the concentration of alanine is 6.3 mM; wherein the concentration of arginine is 5.8 mM; and wherein the concentration of tyrosine is 1.2 mM.

In some embodiments of the formulation, the therapeutically effective combination of free amino acids consists essentially of or consists of a therapeutically effective amount of free amino acids of proline, aspartic acid, serine, threonine, alanine, arginine, and tyrosine.

In some embodiments of the formulation, the therapeutically effective combination of free amino acids consists essentially of or consists of a therapeutically effective amount of free amino acids of proline, aspartic acid, serine, threonine, alanine, arginine, and tyrosine, wherein the concentration of proline is 11-13 mM; wherein the concentration of aspartic acid is 14-18 mM; wherein the concentration of serine is 4-6 mM; wherein the concentration of threonine is 4-6 mM; wherein the concentration of alanine is 3-5 mM; wherein the concentration of arginine is 4-7 mM; and wherein the concentration of tyrosine is 0.6-0.9 mM.

In some embodiments of the formulation, the therapeutically effective combination of free amino acids consists essentially of or consists of a therapeutically effective amount of free amino acids of proline, aspartic acid, serine, threonine, alanine, arginine, and tyrosine, wherein the concentration of proline is 12.3 mM; wherein the concentration of aspartic acid is 16.3 mM; wherein the concentration of serine is 4.8 mM; wherein the concentration of threonine is 5.3 mM; wherein the concentration of alanine is 4.3 mM; wherein the concentration of arginine is 5.8 mM; and wherein the concentration of tyrosine is 0.8 mM.

In some embodiments of the formulation, the formulation further comprises a pharmaceutically acceptable carrier, buffer, electrolyte, adjuvant, excipient, or water.

In some embodiments of the formulation, the formulation is sterile.

In some embodiments of the formulation, at least one of the free amino acids or each of the free amino acids comprises L-amino acids.

In some embodiments of the formulation, the formulation does not comprise monosaccharide glucose, at least one glucose-containing disaccharide, or any combination thereof.

In some embodiments of the formulation, the formulation is a pharmaceutical formulation.

In some embodiments of the formulation, the formulation is formulated for administration by a parenteral, pulmonary, inhalation, intranasal, enteral, intravenous, anal, or sublingual route.

In some embodiments of the formulation, the formulation is formulated for oral administration.

In some embodiments of the formulation, the subject is a mammal. In some embodiments of the formulation, the mammal is a human, cat, dog, pig, horse, cow, sheep, or goat. In some embodiments of the formulation, the mammal is a human. In some embodiments of the formulation, the human is equal to or less than 5 years old; or the human is equal to or greater than 70 years old.

In some embodiments of the formulation, the diarrhea is associated with an infection by bacteria that produce a secretagogue in the subject.

In some embodiments of the formulation, the bacteria comprise at least one of an enterotoxin-producing bacteria or an enterotoxigenic bacteria, or any combination thereof. In some embodiments of the formulation, the enterotoxin-producing bacteria comprises *Vibrio cholerae, Staphylococcus aureus, Bacillus cereus, Clostridium difficile, Clostridium perfringens, Staphylococcus aureus, Yersinia enterocolitica, Shigella dysenteriae*, or an enterotoxigenic *Escherichia coli*, or any combination thereof.

In some embodiments of the formulation, the at least one symptom associated with diarrhea comprises at least one of loose, watery stools; abdominal cramps; abdominal pain;

fever; blood in the stool; mucus in the stool; bloating; or nausea; or any combination thereof.

In some embodiments of the formulation, reducing the at least one symptom associated with diarrhea comprises a reduction in at least one of volume of loose, watery stools per day; or frequency of loose, watery stools per day; or a combination thereof.

In some embodiments of the formulation, the formulation is formulated for use as a medicament for the treatment of diarrhea.

In some embodiments of the formulation, a method for treating diarrhea in a subject in need thereof is presented, the method comprising: administering to the subject in need thereof a formulation described herein, wherein the administering reduces at least one symptom associated with diarrhea in the subject.

In some embodiments, a formulation is presented, wherein the formulation comprises a therapeutically effective combination of free amino acids: the free amino acids consisting essentially of or consisting of a therapeutically effective amount of free amino acids of proline and aspartic acid; and a therapeutically effective amount of at least one of free amino acids of serine, threonine, glycine, alanine, arginine, or tyrosine, or any combination thereof; and optionally, free amino acids of asparagine; or optionally, monosaccharide glucose, at least one glucose-containing disaccharide, or any combination thereof, wherein the total concentration of the monosaccharide glucose, the at least one glucose-containing disaccharide, or any combination thereof is equal to or less than 90 mM; or optionally, at least one pharmaceutically acceptable carrier, buffer, electrolyte, adjuvant, excipient, or water, or any combination thereof; or any combination thereof and wherein the therapeutically effective combination of free amino acids is sufficient to reduce at least one symptom associated with diarrhea. In some embodiments thereof, the therapeutically effective combination of free amino acids consists essentially of or consists of a therapeutically effective amount of free amino acids of proline, aspartic acid, serine, threonine, glycine, alanine, arginine, and tyrosine.

In some embodiments thereof, the therapeutically effective combination of free amino acids consists essentially of or consists of a therapeutically effective amount of free amino acids of proline, aspartic acid, serine, threonine, glycine, alanine, arginine, and tyrosine, wherein the concentration of proline is 8-10 mM; wherein the concentration of aspartic acid is 9-11 mM;

wherein the concentration of serine is 9-11 mM; wherein the concentration of threonine is 7-9 mM;

wherein the concentration of glycine is 6-8 mM;

wherein the concentration of alanine is 5-6 mM; wherein the concentration of arginine is 6-7 mM;

and wherein the concentration of tyrosine is 0.8-1.2 mM.

In some embodiments thereof, the therapeutically effective combination of free amino acids consists essentially of or consists of a therapeutically effective amount of free amino acids of proline, aspartic acid, serine, threonine, glycine, alanine, arginine, and tyrosine, wherein the concentration of proline is 9 mM; wherein the concentration of aspartic acid is 10 mM;

wherein the concentration of serine is 10 mM; wherein the concentration of threonine is 8 mM;

wherein the concentration of glycine is 7 mM; wherein the concentration of alanine is 5.3 mM;

wherein the concentration of arginine is 6.7 mM; and wherein the concentration of tyrosine is 1.2 mM.

In some embodiments thereof, the therapeutically effective combination of free amino acids consists essentially of or consists of a therapeutically effective amount of free amino acids of proline, aspartic acid, serine, threonine, glycine, alanine, arginine, and tyrosine, wherein the concentration of proline is 9-11 mM; wherein the concentration of aspartic acid is 15-17 mM; wherein the concentration of serine is 7-9 mM; wherein the concentration of threonine is 3-5 mM; wherein the concentration of glycine is 5-7 mM; wherein the concentration of alanine is 5-7 mM; wherein the concentration of arginine is 5-7 mM; and wherein the concentration of tyrosine is 0.8-1.2 mM.

In some embodiments thereof, the therapeutically effective combination of free amino acids consists essentially of or consists of a therapeutically effective amount of free amino acids of proline, aspartic acid, serine, threonine, glycine, alanine, arginine, and tyrosine, wherein the concentration of proline is 10 mM; wherein the concentration of aspartic acid is 15.9 mM; wherein the concentration of serine is 8 mM; wherein the concentration of threonine is 4.3 mM; wherein the concentration of glycine is 5.7 mM; wherein the concentration of alanine is 6.3 mM; wherein the concentration of arginine is 5.8 mM; and wherein the concentration of tyrosine is 1.2 mM.

In some embodiments thereof, the therapeutically effective combination of free amino acids consists essentially of or consists of a therapeutically effective amount of free amino acids of proline, aspartic acid, serine, threonine, alanine, arginine, and tyrosine.

In some embodiments thereof, the therapeutically effective combination of free amino acids consists essentially of or consists of a therapeutically effective amount of free amino acids of proline, aspartic acid, serine, threonine, alanine, arginine, and tyrosine, wherein the concentration of proline is 11-13 mM; wherein the concentration of aspartic acid is 14-18 mM; wherein the concentration of serine is 4-6 mM; wherein the concentration of threonine is 4-6 mM; wherein the concentration of alanine is 3-5 mM; wherein the concentration of arginine is 4-7 mM; and wherein the concentration of tyrosine is 0.6-0.9 mM.

In some embodiments thereof, the therapeutically effective combination of free amino acids consists essentially of or consists of a therapeutically effective amount of free amino acids of proline, aspartic acid, serine, threonine, alanine, arginine, and tyrosine, wherein the concentration of proline is 12.3 mM; wherein the concentration of aspartic acid is 16.3 mM; wherein the concentration of serine is 4.8 mM; wherein the concentration of threonine is 5.3 mM; wherein the concentration of alanine is 4.3 mM; wherein the concentration of arginine is 5.8 mM; and wherein the concentration of tyrosine is 0.8 mM.

BRIEF DESCRIPTION OF THE DRAWINGS

Some embodiments of the disclosure are herein described, by way of example only, with reference to the accompanying drawings. With specific reference now to the drawings in detail, it is stressed that the embodiments shown are by way of example and for purposes of illustrative discussion of embodiments of the disclosure. In this regard, the description taken with the drawings makes apparent to those skilled in the art how embodiments of the disclosure may be practiced.

DETAILED DESCRIPTION

Figure 1:
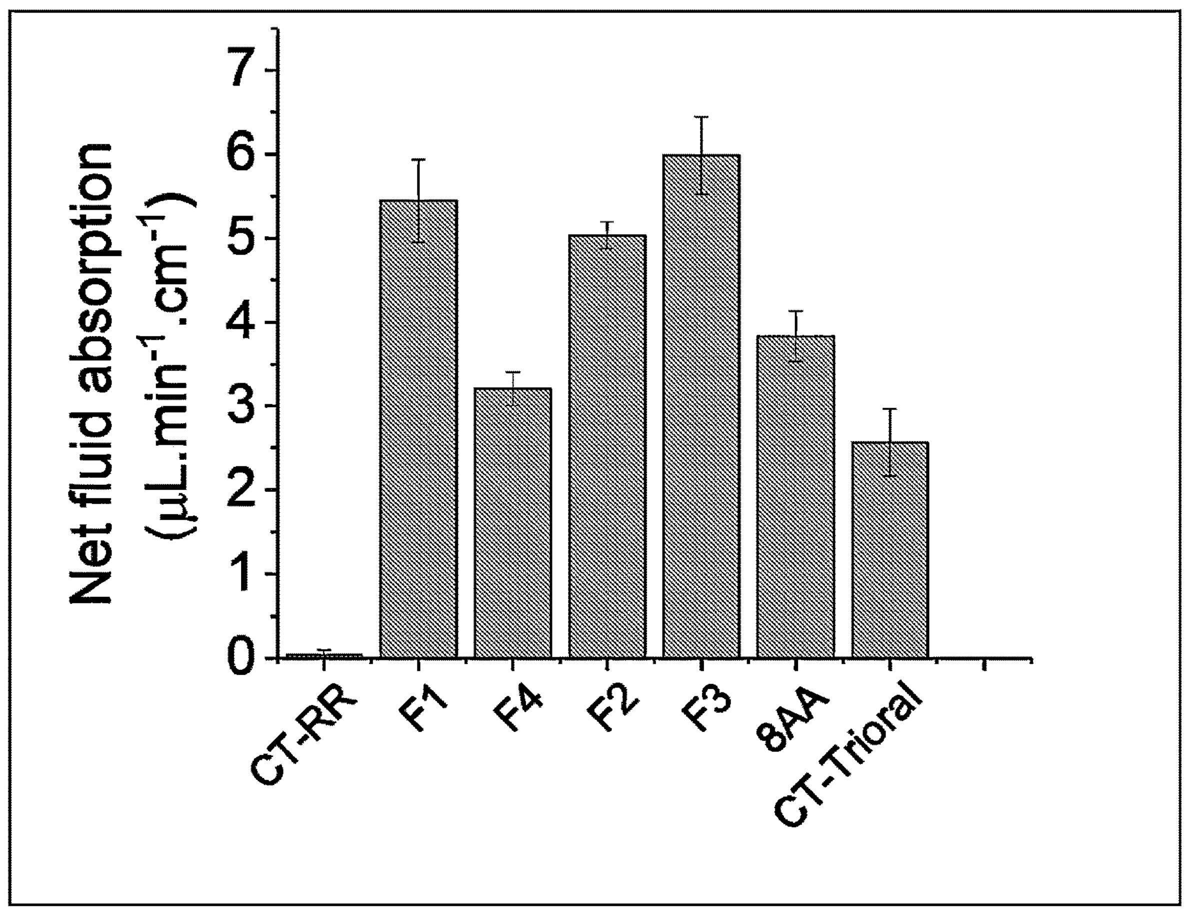
FIG. 1: Net fluid absorption in the presence of the indicated formulations in the presence of cholera toxin as determined by perfusion assay. Cholera toxin (CT); Ringer's solution (RR); Trioral (WHO oral rehydration solution).

Among those benefits and improvements that have been disclosed, other objects and advantages of this disclosure will become apparent from the following description taken in conjunction with the accompanying figures. Detailed embodiments of the present disclosure are disclosed herein; however, it is to be understood that the disclosed embodiments are merely illustrative of the disclosure that may be embodied in various forms. In addition, each of the examples given regarding the various embodiments of the disclosure which are intended to be illustrative, and not restrictive.

The prevalence of diarrheal disease is correlated closely with climate and economic development. Developing countries in sub-Saharan Africa and South Asia tend to have high frequency of diarrheal disease. The major causes of diarrheal diseases in developing countries are infectious, including enterotoxin-producing bacteria, such as *Vibrio cholerae* and enterotoxigenic *Escherichia coli*; viruses, such as rotavirus; enteroinvasive bacteria, such as *Shigella* and *Salmonella*; and parasites, such as *Entamoeba histolytica* and *Cryptosporidium parvum*. *V. cholerae*, for example, causes at least 1-2% of the cases of severe diarrhea observed worldwide.

*Salmonella*-induced enterocolitis is the single most common cause of death from food-borne illnesses associated with viruses, parasites, or bacteria in the United States. The serotype associated most frequently with this diarrheal disease syndrome in the United States is *Salmonella* serotype *Typhimurium*, which accounts for 26% of all *Salmonella* isolates reported to the Centers for Disease Control. *Salmonella typhimurium* invades intestinal mucosa but does not elaborate a traditional enterotoxin. It elicits ileal secretion by causing alterations in active sodium and chloride transport mechanisms. Typhoid fever, which is caused by the human-adapted *S. enterica* serotype *Typhi*, causes typhoid fever.

Typhoid fever affects millions of people globally each year, with a morbidity rate of approximately 200,000 people per year.

Exemplary oral rehydration solutions comprising select amino acids (AA-ORS) described herein exhibit surprising combinatorial activities with respect to net chloride, sodium, and fluid absorption as reflected by statistically significant and superior therapeutic properties when compared to WHO-ORS in animal model systems of human intestinal response, whether compared in the absence (normal, healthy condition) or presence of secretagogue (diseased condition). The animal model systems comprise normal, healthy (unexposed to toxin) and cholera toxin (CT)-exposed mouse and rat small intestines, thereby recapitulating human intestinal response in the absence or presence of a secretagogue, respectively.

Exemplary AA-ORS described herein exhibited enhanced electrolyte absorption. Combinations of amino acids in each of the exemplary AA-ORS exhibited synergistic effect with respect to a variety of criteria, including net fluid absorption. See, for example, FIGS. 1-3. As described herein, exemplary AA-ORS formulations (e.g., F1, F2, F3, and F4) were tested in an anesthetized rat model for intestinal lumen perfusion in the presence of CT. Lumen perfusion studies showed that F3 exhibited advantageous properties with respect to promoting net fluid absorption as reflected by a statistically significant increase of ~2.3 fold in net fluid absorption in the presence of CT when compared to that of WHO-ORS in the presence of CT. F1 and F2 also exhibited advantageous properties with respect to promoting net fluid absorption as reflected by statistically significant increases of ~2.0 fold in net fluid absorption in the presence of CT when compared to that of WHO-ORS in the presence of CT. See, for example, FIG. 2.

Lumen perfusion studies also showed that F3 exhibited advantageous properties with respect to promoting net fluid absorption as reflected by a statistically significant increase of 56% in net fluid absorption in the presence of CT when compared to that of 8AA in the presence of CT. F1 also exhibited advantageous properties with respect to promoting net fluid absorption as reflected by a statistically significant increase of 42% in net fluid absorption in the presence of CT when compared to that of 8AA in the presence of CT. F2 also exhibited advantageous properties with respect to promoting net fluid absorption as reflected by a statistically significant increase of 31% in net fluid absorption in the presence of CT when compared to that of 8AA in the presence of CT. In contrast, F4, which contains 8 free amino acids (many of which are in common with F1, F2, and F3) conferred statistically significant lower net fluid absorption relative to 8AA. See FIG. 1.

Each of exemplary formulations F1, F2, and F3 comprise the following free amino acids: proline, aspartic acid, serine, arginine, tyrosine, threonine, and alanine. F2 and F3 comprise free amino acids of proline, aspartic acid, serine, arginine, tyrosine, threonine, alanine, and glycine. F1 comprises free amino acids of proline, aspartic acid, serine, arginine, tyrosine, threonine, alanine, and asparagine.

Figure 2:
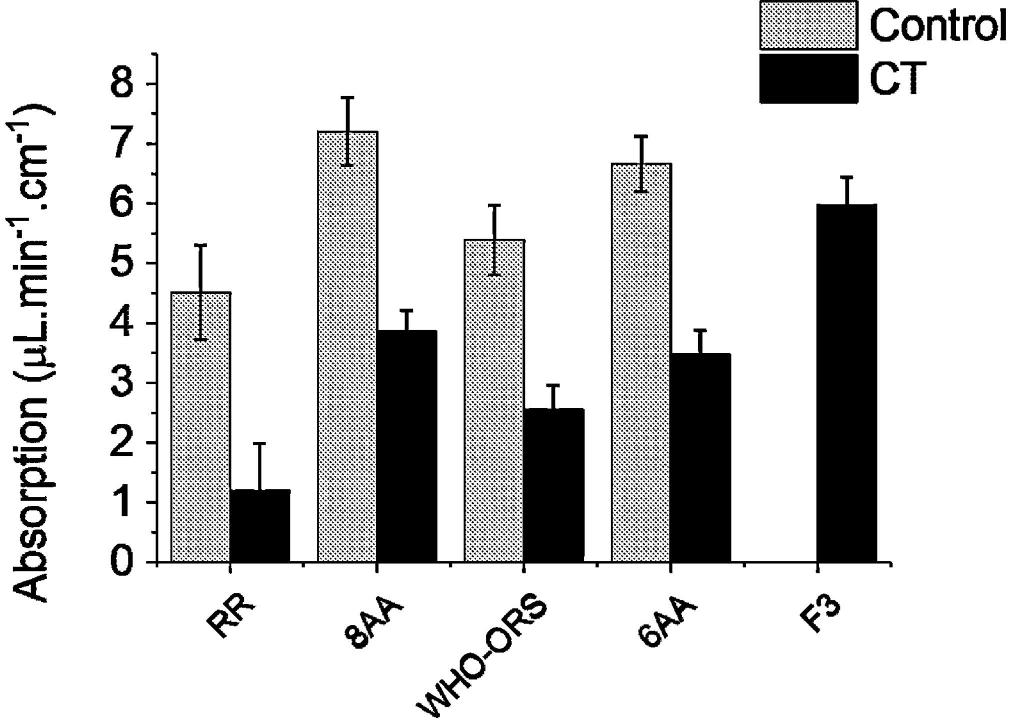
FIG. 2: Effect of the presence or absence of secretagogue on net fluid absorption in the presence of the indicated formulations. RR: Ringer solution with 105 mM Na, 241 mOsms, pH 4.049 [n=6 (Control) & n=4 (cholera toxin (CT))]; 8AA: aspartic acid, glycine, valine, isoleucine, threonine, tyrosine, serine and lysine, 67 mM Na, 243 mOsms, pH 3.82 [n=6 (Control) & n=8 (CT)]; WHO ORS (Trioral): 75 mM Na, 75 mM glucose, 221-225 mOsms, pH 7.5-7.8 [n=6 (Control) & n=8 (CT)]; 6AA: Aspartic acid, valine, isoleucine, threonine, tyrosine, and lysine, 67 mM Na, 245 mOsms, pH 3.7 [n=6 (Control) & n=9 (CT)]; F3: Aspartic acid, glycine, threonine, tyrosine, serine, proline, alanine and arginine, 67 mM Na, 221 mOsmos, pH 4.096 [n=0 (Control) & n=4 (CT)].
Figure 3:
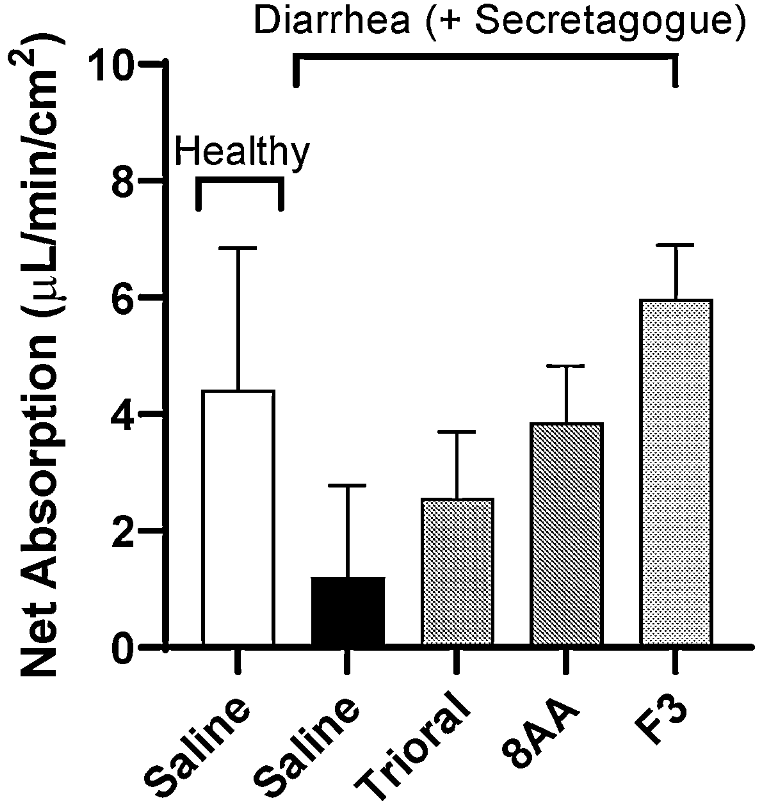
FIG. 3: Effect of a secretagogue on net fluid absorption in the presence of the indicated formulations. Saline: Ringer solution with 105 mM Na, 241 mOsms, pH 4.049 [healthy (absence of secretagogue; Diarrhea+secretagogue (in presence of secretogogue)]; Trioral (WHO ORS): 75 mM Na, 75 mM glucose, 221-225 mOsms, pH 7.5-7.8 (in presence of secretogogue); 8AA: aspartic acid, glycine, valine, isoleucine, threonine, tyrosine, serine and lysine, 67 mM Na, 243 mOsms, pH 3.82 (in presence of secretogogue)]; F3: Aspartic acid, glycine, threonine, tyrosine, serine, proline, alanine and arginine, 67 mM Na, 221 mOsmos, pH 4.096 (in presence of secretogogue).

The results presented in FIGS. 1-3 demonstrate that factors such as the complement of free amino acids present in an amino acid formulation and the concentrations thereof contribute synergistically to the activity of amino acid formulations with respect to net fluid absorption conferred thereby.

In some embodiments, a concentration of each of the free amino acids present in the formulation ranges from 0.1 mM to 20 mM or 0.5 mM to 20 mM. In some embodiments, a concentration of each of the free amino acids present in a formulation ranges from 0.1 mM to 17 mM or 0.5 mM to 17 mM. In some embodiments, a concentration of each of the free amino acids present in a formulation ranges from 0.1 mM to 15 mM or 0.5 mM to 15 mM. In some embodiments, a concentration of each of the free amino acids present in the formulation ranges from 0.1 mM to 10 mM or 0.5 mM to 10 mM.

In some embodiments, the pH of a formulation described herein ranges from 2.5 to 8.0, 3.0 to 8.0, 3.0 to 4.5, 3.0 to 4.2, 3.4 to 4.2, 3.5 to 4.2, 3.5 to 4.1, 3.5 to 8.0, 4.0 to 8.0, 4.5 to 8.0, 4.5 to 6.5, 5.5 to 6.5, 5.0 to 8.0, 5.5 to 8.0, 6.0 to 8.0, 6.5 to 8.0, 7.0 to 8.0, or 7.5 to 8.0. In some embodiments, the pH is about 3.7, 3.5, or 4.1.

As used herein, the phrase "reduce at least one symptom associated with the diarrhea" may be used to refer to at least one of a decrease in volume of loose, watery stools per day; or a decrease in frequency of loose, watery stools per day; or a decrease in any combination thereof of 5%, 10%, 15%, 20%, 25%, 30%, 35%, 40%, 45%, 50%, 55%, 60%, 65%, 70%, 75%, 80%, 85%, 90%, 95%, or 100%.

As used herein, the term "bacterial secretagogue" may be used to refer to a substance produced by a bacteria that promotes anion secretion from the intestinal crypt.

As described herein, a reduction in at least one symptom associated with the diarrhea may be determined by, for example, at least one of measuring the volume and/or frequency of loose, watery stools per day using standard volumetric measuring devices (e.g., sample collecting containers with tared measurements for quantitation) or by counting the number of loose, watery stools per day and recording same by some standard means, or any combination thereof.

The present inventors have established model systems in which to evaluate net fluid absorption in the context of a mammalian intestine. More particularly, an anesthetized rat model for intestinal lumen perfusion has been developed that may be performed in the presence or absence of a secretagogue. The ability to perform the assay in the presence or absence of a secretagogue simulates conditions that mimic those of intestines of subjects afflicted by diarrheal disease caused by infection with bacteria, irrespective of the bacteria's ability to produce a secretagogue. Since dehydration is a serious and life-threatening consequence of diarrheal disease, quantitation of increases in net fluid absorption conferred by formulations described herein in perfusion assays reflects therapeutic benefit conferred by these formulations when used to treat subjects afflicted by diarrheal disease.

Based on results presented herein, F1, F2, and F3 were selected as exemplary formulations that exhibit the ability to increase net fluid absorption relative to a negative control solution (Ringer solution) and exhibit a statistically significant increase in net fluid absorption when compared to WHO-ARS (Trioral), which is the standard of care for the treatment of diarrheal disease worldwide. The superiority of each of F1, F2, and F3 relative to Trioral with respect to the ability to increase net fluid absorption is noteworthy under all experimental conditions tested (irrespective of secretagogue status), but is particularly pronounced in the presence of secretagogue. See, for example, FIGS. 1 and 2. As detailed herein, performing net fluid absorption assays in the presence of secretagogue (e.g., forskolin or cholera toxin) serves as a model which simulates conditions in the intestines of subjects afflicted by diarrheal disease caused by infection with bacteria that produce a secretagogue.

As described herein, an increase in net fluid absorption may be determined by, for example, measuring net fluid absorption in a perfusion assay using a mammalian lumen intestinal segment and a quantitative measurement made for a particular formulation may be compared to net fluid absorption of, for example, a negative control solution in the perfusion assay to determine percent increase relative to the negative control solution. A quantitative measurement made for a particular formulation may, furthermore, be compared to net fluid absorption of, for example, a positive control solution in the perfusion assay as a relative comparator predictive of efficacy.

Throughout the specification and claims, the following terms take the meanings explicitly associated herein, unless the context clearly dictates otherwise. The phrases "in one embodiment," "in an embodiment," and "in some embodiments" as used herein do not necessarily refer to the same embodiment(s), though it may. Furthermore, the phrases "in another embodiment" and "in some other embodiments" as used herein do not necessarily refer to a different embodiment, although it may. All embodiments of the disclosure are intended to be combinable without departing from the scope or spirit of the disclosure.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

An "effective amount" or "effective dose" of an agent (or composition containing such agent) refers to the amount sufficient to achieve a desired biological and/or pharmacological effect, e.g., when delivered to a cell or organism according to a selected administration form, route, and/or schedule. The phrases "effective amount" and "therapeutically effective amount" are used interchangeably. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered to a subject in a single dose, or through use of multiple doses, in various embodiments. In some embodiments, an effective amount is an amount that increases net fluid absorption in a cell. In some embodiments, an effective amount is an amount that increases net fluid absorption in a subject in need thereof. In some embodiments thereof, an effective amount is an amount that increases net fluid absorption in the intestines of a subject in need thereof. In some embodiments, an effective amount is an amount that reduces at least one symptom of a diarrhea associated with decreased fluid absorption. In some embodiments thereof, an effective amount is an amount that reduces at least one symptom of a diarrhea associated with decreased fluid absorption in the intestines of a subject. In some embodiments thereof, an effective amount is an amount that reduces at least one symptom of a diarrhea associated with a bacterial infection in the intestines of a subject. In some embodiments thereof, an effective amount is an amount that reduces at least one symptom of a diarrhea associated with a bacterial infection in the intestines of a subject, wherein the bacterial infection is associated with bacteria that produce a secretagogue. In some embodiments thereof, an effective amount is an amount that reduces at least one symptom of a diarrhea associated with a bacterial infection in the intestines of a subject, wherein the bacterial infection is associated with bacteria that do not produce a secretagogue.

"Treat," "treatment", "treating" and similar terms as used herein in the context of treating a subject refer to providing medical and/or surgical management of a subject. Treatment may include, but is not limited to, administering an agent or composition (e.g., a pharmaceutical composition) to a subject. The term "treatment" or any grammatical variation thereof (e.g., treat, treating, and treatment etc.), as used herein, includes but is not limited to, alleviating at least one symptom of a disease or condition; and/or reducing, suppressing, inhibiting, lessening, or affecting the progression, severity, and/or scope of a disease or condition.

The effect of treatment may also include reducing the likelihood of occurrence or recurrence of the disease or at least one symptom or manifestation of the disease. A therapeutic agent may be administered to a subject who has a disease or is at increased risk of developing a disease relative to a member of the general population. In some embodiments, a therapeutic agent may be administered to a subject who has had a disease but no longer shows evidence of the disease. The agent may be administered, e.g., to reduce the likelihood of recurrence of the disease. A therapeutic agent may be administered prophylactically, i.e., before development of at least one symptom or manifestation of a disease.

"Prophylactic treatment" refers to providing medical and/or surgical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease).

The term "amelioration" or any grammatical variation thereof (e.g., ameliorate, ameliorating, and amelioration, etc.), as used herein, includes, but is not limited to, delaying the onset, or reducing the severity of a disease or condition (e.g., disease or disorder associated with decreased fluid absorption or a complication thereof). Amelioration, as used herein, does not require the complete absence of symptoms.

The terms "condition," "disease," and "disorder" are used interchangeably.

A "subject" may be any vertebrate organism in various embodiments. A subject may be an individual to whom an agent is administered, e.g., for experimental, diagnostic, and/or therapeutic purposes or from whom a sample is obtained or on whom a procedure is performed. In some embodiments a subject is a mammal, e.g., humans; a non-human primate (e.g., apes, chimpanzees, orangutans, monkeys); or domesticated animals such as dogs, cats, rabbits, cattle, oxen, horses (including, e.g., foals), pigs, sheep, goats, llamas, mice, and rats. In some embodiments, the subject is a human. The human or other mammal may be of either sex and may be at any stage of development. In some embodiments, the human or other mammal is a baby [e.g., a human baby; an infant (human baby from birth to 1 year old], a juvenile (e.g., a toddler or young child under the age of 5 years), or an elderly subject (e.g., a human over the age of 70 years). In some embodiments, the subject has been diagnosed with diarrhea, which is associated with decreased fluid absorption.

By "negligible amount" it is meant that the free amino acid present does not increase fluid absorption in, for example, an intestinal lumen perfusion assay. Or, in some embodiments, even if the free amino acid is present in the formulation, it is not present in an amount that would affect fluid absorption in, for example, an intestinal lumen perfusion assay or the therapeutic effect of treating a subject in need thereof. In some embodiments, a negligible amount is an amount wherein the total concentration of the free amino acid is less than 100 mg/l, 50 mg/l, 10 mg/l, 5 mg/l, 1 mg/l, 0.5 mg/l, 0.1 mg/1, or 0.01 mg/l. In some embodiments, a negligible amount is an amount wherein the total concentration of the free amino acid is less than 100 mg/l. In some embodiments, a negligible amount is an amount wherein the total concentration of the free amino acid is less than 50 mg/l. In some embodiments, a negligible amount is an amount wherein the total concentration of the free amino acid is less than 10 mg/l. In some embodiments, a negligible amount is an amount wherein the total concentration of the free amino acid is less than 5 mg/l. In some embodiments, a negligible amount is an amount wherein the total concentration of the free amino acid is less than 1 mg/l. In some embodiments, a negligible amount is an amount wherein the total concentration of the free amino acid is less than 0.5 mg/l. In some embodiments, a negligible amount is an amount wherein the total concentration of the free amino acid is less than 0.1 mg/l. In some embodiments, a negligible amount is an amount wherein the total concentration of the free amino acid is less than 0.01 mg/l.

The term "amino acid" encompasses all known amino acids comprising an amine ($—NH_2$) functional group, a carboxyl (—COOH) functional group, and a side chain ("R") group specific to each amino acid. "Amino acids" encompasses the 21 amino acids encoded by the human genome (i.e., proteinogenic amino acids), amino acids encoded or produced by bacteria or single-celled organisms, and naturally derived amino acids. For the purposes of this disclosure, the conjugate acid form of amino acids with basic side chains (arginine, lysine, and histidine) or the conjugate base form of amino acids with acidic side chains (aspartic acid and glutamic acid) are essentially the same, unless otherwise noted. "Amino acids" also encompass derivatives thereof that retain substantially the same activity in terms of increasing fluid absorption in, for example, an intestinal lumen perfusion assay. The derivatives may be, for example, enantiomers, and include both the D- and L-forms of the amino acids. The derivatives may be derivatives of "natural" or "non-natural" amino acids (e.g., β-amino acids, homo-amino acids, proline derivatives, pyruvic acid derivatives, β-substituted alanine derivatives, glycine derivatives, ring-substituted tyrosine derivatives, ring-substituted phenylalanine derivatives, linear core amino acids, and N-methyl amino acids), for example, selenocysteine, pyrrolysine, iodotyrosine, norleucine, or norvaline. Other amino acid derivatives include, but are not limited to, those that are synthesized by, for example, acylation, methylation, glycosylation, and/or halogenation of the amino acid. These include, for example, β-methyl amino acids, C-methyl amino acids, and N-methyl amino acids. The amino acids described herein may be present as free amino acids. The term "free amino acid" refers to an amino acid that is not part of a peptide or polypeptide (e.g., is not connected to another amino acid through a peptide bond). A free amino acid is free in solution (as opposed to being linked to at least one other amino acid via, for example, a dipeptide bond), but may be associated with a salt or other component in solution.

As used herein, the term "salt" refers to any and all salts and encompasses pharmaceutically acceptable salts.

The term "carrier" may refer to any diluent, adjuvant, excipient, or vehicle with which a formulation described herein is administered. Examples of suitable pharmaceutical carriers are described in *Remington's Essentials of Pharmaceuticals,* 21$^{st}$ ed., Ed. Felton, 2012, which is herein incorporated by reference.

Exemplary salts for inclusion in a formulation described herein include sodium chloride, potassium chloride, calcium chloride, magnesium chloride, or tri-sodium citrate, sodium bicarbonate, sodium gluconate phosphate buffers using mono, di or tri-sodium phosphate or any combination thereof.

Exemplary diluents include calcium carbonate, sodium carbonate, calcium phosphate, dicalcium phosphate, calcium sulfate, calcium hydrogen phosphate, cellulose, microcrystalline cellulose, kaolin, sodium chloride, and mixtures thereof.

Pharmaceutically acceptable excipients used in the manufacture of pharmaceutical formulations described herein include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, and perfuming agents may also be present in the composition.

The exact amount of an amino acid formulation or composition required to achieve an effective amount will vary from subject to subject, depending, for example, on species, age, and general condition of a subject, severity of the side effects or disorder, mode of administration, and the like. An effective amount may be included in a single dose (e.g., single oral dose) or multiple doses (e.g., multiple oral doses). In some embodiments, when multiple doses are administered to a subject or applied to a tissue or cell, any two doses of the multiple doses include different or substantially the same amounts of an amino acid composition described herein. In some embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In some embodiments, the frequency of administering the multiple doses to the subject or applying the multiple doses to the tissue or cell is one dose per day. In some embodiments, the frequency of administering the multiple doses to the subject or applying the multiple doses to the tissue or cell is two doses per day. In some embodiments, the frequency of administering the multiple doses to the subject or applying the multiple doses to the tissue or cell is three doses per day. In some embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In some embodiments, the duration between the first dose and last dose of the multiple doses is three months, six months, or one year. In some embodiments, the duration between the first dose and last dose of the multiple doses is the lifetime of the subject, tissue, or cell.

In some embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, between 1 g and 10 g, between 1 g and 15 g, or between 1 g and 20 g, inclusive, of an amino acid composition described herein. In some embodiments, a dose described herein includes independently between 1 mg and 3 mg, inclusive, of an amino acid composition described herein. In some embodiments, a dose described herein includes independently between 3 mg and 10 mg, inclusive, of an amino acid composition described herein. In some embodiments, a dose described herein includes independently between 10 mg and 30 mg, inclusive, of an amino acid composition described herein. In some embodiments, a dose described herein includes independently between 30 mg and 100 mg, inclusive, of an amino acid composition described herein.

Dose ranges as described herein provide guidance for the administration of pharmaceutical compositions described herein to an adult. The amount to be administered to, for example, a child or an adolescent can be determined by a medical practitioner or person skilled in the art and may be lower or the same as that administered to an adult.

All prior patents, publications, and test methods referenced herein are incorporated by reference in their entireties.

DETAILED DESCRIPTION OF SOME EMBODIMENTS

In some embodiments, the composition comprises, consists essentially of, or consists of free amino acids of proline (P) and aspartic acid (D) and free amino acids of at least one of serine (S), threonine (T), glycine (G), alanine (A), arginine (R), or tyrosine (Y), and optionally, asparagine (N). The different combinations of this embodiment are presented in List 1 as follows: Eight AA sets: P, D, S, T, G, A, R, and Y. In some embodiments thereof, the composition comprises, consists essentially of, or consists of free amino acids of P, D, S, T, G, A, R, and Y (F3 and F2). In some embodiments thereof, the composition comprises, consists essentially of, or consists of free amino acids of P, D, S, T, N, A, R, and Y (8AA-OP). Seven AA subsets: P, D, S, T, G, A, and R; P, D, S, T, G, A, and Y; P, D, S, T, G, R, and Y; P, D, S, T, A, R, and Y; P, D, S, G, A, R, and Y; and P, D, T, G, A, R, and Y. In embodiments thereof, the composition comprises, consists essentially of, or consists of free amino acids of P, D, S, T, G, A, and R; P, D, S, T, G, A, and Y; P, D, S, T, G, R, and Y; P, D, S, T, A, R, and Y; P, D, S, G, A, R, and Y; or P, D, T, G, A, R, and Y. In some embodiments thereof, N may be substituted for G. Six AA subsets: P, D, S, T, G, and A; P, D, S, T, G, and R; P, D, S, T, G, and Y; P, D, S, T, A, and R; P, D, S, T, A, and Y; P, D, S, T, R, and Y; P, D, S, G, A, and R; P, D, S, G, A, and Y; P, D, S, G, R, and Y; P, D, S, A, R, and Y; P, D, T, G, A, and R; P, D, T, G, A, and Y; P, D, T, G, R, and Y; P, D, T, A, R, and Y; and P, D, G, A, R, and Y. In embodiments thereof, the composition comprises, consists essentially of, or consists of free amino acids of P, D, S, T, G, and A; P, D, S, T, G, and R; P, D, S, T, G, and Y; P, D, S, T, A, and R; P, D, S, T, A, and Y; P, D, S, T, R, and Y; P, D, S, G, A, and R; P, D, S, G, A, and Y; P, D, S, G, R, and Y; P, D, S, A, R, and Y; P, D, T, G, A, and R; P, D, T, G, A, and Y; P, D, T, G, R, and Y; P, D, T, A, R, and Y; or P, D, G, A, R, and Y. In some embodiments thereof, N may be substituted for G. Five AA subsets: P, D, S, T, and G; P, D, S, T, and A; P, D, S, T, and R; P, D, S, T, and Y; P, D, S, G, and A; P, D, S, G, and R; P, D, S, G, and Y; P, D, S, A, and R; P, D, S, A, and Y; P, D, S, R, and Y; P, D, T, G, and A; P, D, T, G, and R; P, D, T, G, and Y; P, D, T, A, and R; P, D, T, A, and Y; P, D, T, R, and Y; P, D, G, A, and R; P, D, G, A, and Y; P, D, G, R, and Y; and P, D, A, R, and Y. In embodiments thereof, the composition comprises, consists essentially of, or consists of free amino acids of P, D, S, T, and G; P, D, S, T, and A; P, D, S, T, and R; P, D, S, T, and Y; P, D, S, G, and A; P, D, S, G, and R; P, D, S, G, and Y; P, D, S, A, and R; P, D, S, A, and Y; P, D, S, R, and Y; P, D, T, G, and A; P, D, T, G, and R; P, D, T, G, and Y; P, D, T, A, and R; P, D, T, A, and Y; P, D, T, R, and Y; P, D, G, A, and R; P, D, G, A, and Y; P, D, G, R, and Y; or P, D, A, R, and Y. In some embodiments thereof, N may be substituted for G. Four AA subsets: P, D, S, and T; P, D, S, and G; P, D, S, and A; P, D, S, and R; P, D, S, and Y; P, D, T, and G; P, D, T, and A; P, D, T, and R; P, D, T, and Y; P, D, G, and A; P, D, G, and R; P, D, G, and Y; P, D, A, and R; P, D, A, and Y; and P, D, R, and Y. In embodiments thereof, the composition comprises, consists essentially of, or consists of free amino acids of P, D, S, and T; P, D, S, and G; P, D, S, and A; P, D, S, and R; P, D, S, and Y; P, D, T, and G; P, D, T, and A; P, D, T, and R; P, D, T, and Y; P, D, G, and A; P, D, G, and R; P, D, G, and Y; P, D, A, and R; P, D, A, and Y; or P, D, R, and Y. In some embodiments thereof, N may be substituted for G. Three AA subsets: P, D, and S; P, D, and T; P, D, and G; P, D, and A; and P, D, and R. In embodiments thereof, the composition comprises, consists essentially of, or consists of free amino acids of P, D, and S; P, D, and T; P, D, and G; P, D, and A; or P, D, and R. In some embodiments thereof, N may be substituted for G.

Accordingly, formulations (e.g., pharmaceutical formulations) comprising the select eight amino acids (P, D, S, T, G, A, R, and Y) in F3 and F2 and subsets thereof comprising three, four, five, six, or seven amino acid subsets of the select eight amino acids and uses thereof for increasing net fluid absorption in intestines of a subject in need thereof and/or treating diarrhea associated with decreased fluid absorption and for preparing medicaments for treating diarrhea associated with decreased fluid absorption are encompassed herein. In some embodiments, the diarrhea is caused by bacteria that produce a secretagogue. In some embodiments, N may be substituted for G in formulations described herein. The above reasoning is equally applied to any combination of two (P, D), three, four, five, six, or seven amino acid subsets of the select eight amino acids (P, D, S, T, G, A, R, and Y) described herein.

Further to the above, formulations (e.g., pharmaceutical formulations) comprising the select eight amino acids (P, D, S, T, N, A, R, and Y) in F1 and subsets thereof comprising three, four, five, six, or seven amino acid subsets of the select eight amino acids and uses thereof for increasing net fluid absorption in intestines of a subject in need thereof and/or treating diarrhea associated with decreased fluid absorption and for preparing medicaments for treating diarrhea associated with decreased fluid absorption are encompassed herein. In some embodiments, the diarrhea is caused by bacteria that produce a secretagogue. The above reasoning is equally applied to any combination of two (P, D), three, four, five, six, or seven amino acid subsets of the select eight amino acids (P, D, S, T, N, A, R, and Y) described herein.

Exemplary formulations described herein are presented in Tables 1-4 below (mmol refers to mmol/Liter in each of the formulations presented below):

TABLE 1

| pH 3.73 | |
|---|---|
| F1 | mmol |
| Aspartic acid | 16.3 |
| Serine | 4.8 |
| Threonine | 5.3 |
| Tyrosine | 0.8 |
| Proline | 12.3 |
| Alanine | 4.3 |
| Arginine | 5.8 |
| Asparagine | 7.7 |
| Perfusion (Mean) | 5.44 |
| SEM | 0.49 |

TABLE 2

| pH 3.532 | |
|---|---|
| F2 | mmol |
| Aspartic acid | 15.9 |
| Serine | 8.0 |
| Threonine | 4.3 |
| Tyrosine | 1.2 |
| Proline | 10.0 |
| Alanine | 6.3 |
| Arginine | 5.8 |
| Glycine | 5.7 |
| Perfusion (Mean) | 5.03 |
| SEM | 0.16 |

TABLE 3

| pH 4.096 | |
|---|---|
| F3 | mmol |
| Aspartic acid | 10 |
| Serine | 10 |
| Threonine | 8 |
| Tyrosine | 1.2 |
| Proline | 9 |
| Alanine | 5.3 |
| Arginine | 6.7 |
| Glycine | 7 |
| Perfusion (Mean) | 5.98 |
| SEM | 0.46 |

TABLE 4

| pH 3.435 | |
|---|---|
| F4 | mmol |
| Aspartic acid | 16.2 |
| Serine | 8 |
| Threonine | 4.6 |
| Tyrosine | 1.2 |
| Proline | 18 |
| Valine | 4.8 |
| Isoleucine | 0.4 |
| Glycine | 4 |
| Perfusion (Mean) | 3.2 |
| SEM | 0.2 |

Several control solutions utilized in experimental results presented herein include:

Negative control—Ringer solution with 105 mM Na, 241 mOsms, pH 4.049

Comparator solution—8AA: aspartic acid, glycine, valine, isoleucine, threonine, tyrosine, serine and lysine, 67 mM Na, 243 mOsms, pH 3.82. Perfusion (Mean)=3.83

Comparator solution—WHO ORS (Trioral): 75 mM Na, 75 mM glucose, 221-225 mOsms, pH 7.5-7.8. Perfusion (Mean)=2.56

Comparator solution—6AA: Aspartic acid, valine, isoleucine, threonine, tyrosine, and lysine, 67 mM Na, 245 mOsms, pH 3.7

F3: Aspartic acid, glycine, threonine, tyrosine, serine, proline, alanine, and arginine (57.2 mM). Na (67 mM), 221 mOsmos, pH 4.096 (- & n=4)

In some embodiments, a formulation described herein may optionally comprises monosaccharide glucose, at least one glucose-containing disaccharide, or any combination thereof, wherein the total concentration of the monosaccharide glucose, the at least one glucose-containing disaccharide, or any combination thereof is equal to or less than 90 mM. In embodiments thereof, monosaccharide glucose, the at least one glucose-containing disaccharide, or any combination thereof is equal to or less than 85 mM; monosaccharide glucose, the at least one glucose-containing disaccharide, or any combination thereof is equal to or less than 80 mM; monosaccharide glucose, the at least one glucose-containing disaccharide, or any combination thereof is equal to or less than 75 mM; monosaccharide glucose, the at least one glucose-containing disaccharide, or any combination thereof is equal to or less than 70 mM; monosaccharide glucose, the at least one glucose-containing disaccharide, or any combination thereof is equal to or less than 65 mM; monosaccharide glucose, the at least one glucose-containing disaccharide, or any combination thereof is equal to or less than 60 mM; monosaccharide glucose, the at least one glucose-containing disaccharide, or any combination thereof is equal to or less than 55 mM; monosaccharide glucose, the at least one glucose-containing disaccharide, or any combination thereof is equal to or less than 50 mM; monosaccharide glucose, the at least one glucose-containing disaccharide, or any combination thereof is equal to or less than 45 mM; monosaccharide glucose, the at least one glucose-containing disaccharide, or any combination thereof is equal to or less than 40 mM; monosaccharide glucose, the at least one glucose-containing disaccharide, or any combination thereof is equal to or less than 35 mM; monosaccharide glucose, the at least one glucose-containing disaccharide, or any combination thereof is equal to or less than 30 mM; monosaccharide glucose, the at least one glucose-containing disaccharide, or any combination thereof is equal to or less than 25 mM; monosaccharide glucose, the at least one glucose-containing disaccharide, or any combination thereof is equal to or less than 20 mM; monosaccharide glucose, the at least one glucose-containing disaccharide, or any combination thereof is equal to or less than 15 mM; monosaccharide glucose, the at least one glucose-containing disaccharide, or any combination thereof is equal to or less than 10 mM; or monosaccharide glucose, the at least one glucose-containing disaccharide, or any combination thereof is equal to or less than 35 mM.

In embodiments thereof, monosaccharide glucose, the at least one glucose-containing disaccharide, or any combination thereof ranges from 10-90 mM; ranges from 10-85 mM; ranges from 10-80 mM; ranges from 10-75 mM; ranges from 10-70 mM; ranges from 10-65 mM; ranges from 10-60 mM; ranges from 10-55 mM; ranges from 10-50 mM; ranges from 10-45 mM; ranges from 10-40 mM; ranges from 10-35 mM; ranges from 10-30 mM; ranges from 10-25 mM; ranges from 10-20 mM; ranges from 5-90 mM; ranges from 5-85 mM; ranges from 5-80 mM; ranges from 5-75 mM; ranges from 5-70 mM; ranges from 5-65 mM; ranges from 5-60 mM; ranges from 5-55 mM; ranges from 5-50 mM; ranges from 5-45 mM; ranges from 5-40 mM; ranges from 5-35 mM; ranges from 5-30 mM; ranges from 5-25 mM; ranges from 5-20 mM; ranges from 1-90 mM; ranges from 1-85 mM; ranges from 1-80 mM; ranges from 1-75 mM; ranges from 1-70 mM; ranges from 1-65 mM; ranges from 1-60 mM; ranges from 1-55 mM; ranges from 1-50 mM; ranges from 1-45 mM; ranges from 1-40 mM; ranges from 1-35 mM; ranges from 1-30 mM; ranges from 1-25 mM; or ranges from 1-20 mM.

In some embodiments, the therapeutic composition does not contain any saccharides, including any mono-, di-, oligo-, polysaccharides, and carbohydrates. In some embodiments, the therapeutic composition does not contain glucose, and/or any di-, oligo, polysaccharides, and carbohydrates that can be hydrolyzed into glucose. In some embodiments, the composition does not contain lactose. In some embodiments, the therapeutic composition does not contain fructose and/or galactose, and/or any di-, oligo, polysaccharides, and carbohydrates that can be hydrolyzed into fructose and/or galactose.

The term "consisting essentially of" as used herein, limits the scope of the ingredients and steps to the specified materials or steps and those that do not materially affect the basic and novel characteristic(s) of the present invention, e.g., compositions and use thereof for the treatment of diarrhea associated with decreased fluid absorption and methods for treating diarrhea associated with decreased fluid absorption. For instance, by using "consisting essentially of" the therapeutic composition does not contain any ingredients not expressly recited in the claims including, but not limited to, free amino acids, di-, oligo, or polypeptides or proteins; and mono-, di-, oligo-, polysaccharides, and carbohydrates that have a direct therapeutic effect on treatment of diarrhea associated with decreased fluid absorption. Within the context of "consisting essentially of", a change in therapeutic effect conferred by an additional ingredient may be determined based on a change in fluid absorption in rat intestinal lumen perfusion assays, wherein an increase or decrease of up to 1%, 2%, 3%, 4%, or 5% can fall within the term "consisting essentially of". Also, by using the term "consisting essentially of" the composition may comprise substances that do not have therapeutic effects on the treatment of diarrhea associated with decreased fluid absorption.

Variations, modifications and alterations to embodiments of the present disclosure described above will make themselves apparent to those skilled in the art. All such variations, modifications, alterations and the like are intended to fall within the spirit and scope of the present disclosure, limited solely by the appended claims.

While several embodiments of the present disclosure have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

Any feature or element that is positively identified in this description may also be specifically excluded as a feature or element of an embodiment of the present as defined in the claims.

The disclosure described herein may be practiced in the absence of any element or elements, limitation or limitations, which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the disclosure.

Exemplary methods include: Electrophysiology techniques: a) Measuring benzamil-sensitive current (electrogenic sodium current mediated by ENaC), bumetanide-sensitive current and transepithelial resistance in Ussing chambers; b) Ussing chamber flux studies using $^{22}Na$ to determine net Na absorption and $^{36}Cl$ for chloride secretion; and c) Permeability assay using fluorescein isothiocyanate (FITC)-dextran (4 KD) added directly to the chamber.

Ussing Chamber—Sodium Flux (General)

Small intestinal mucosal tissues (ileum and jejunum) from 8-week old male Swiss mice were mounted in Ussing chambers containing isotonic Ringer solution, that was bubbled with 95% $O_2$ and 5% $CO_2$ and maintained at 37° C. throughout the experiment. After the tissues were allowed to stabilize, the conductance (G; expressed as $mS/cm^2$) was recorded, and intestinal tissues were paired based on similar conductance. Sodium radioisotope ($^{22}Na$) was added to either the basolateral or apical side of each tissue pair (Hot). Ringer samples were taken every 15 minutes from the contralateral sides (Cold). Sample $^{22}Na$ activity was analyzed using a gamma counter, and unidirectional net sodium flux (Jnet; $\mu eq \cdot cm^2 \cdot h^{-1}$) was calculated.

$$Jnet = \frac{(\text{Cold } CPM2 - \text{Blank}) - [(\text{Cold } CPM1 - \text{Blank}) \times 9/10] \times 5 \times 4 \times 140}{(\text{Hot } CPM - \text{Blank}) \times 10 \times 0.3}$$

[CPM=count per minute, CPM1=previous sample, CPM2=following sample; Blank=no $^{22}Na$ added; 9/10=dilution factor for each sample (0.5 mL to 5 mL); 5=chamber volume (5 mL); 4=time factor (15 min to 60 min); 140=sodium concentration; Hot CPM="Hot" sample activity; Cold CPM="Cold" sample activity; 10=volume factor for Hot sample (0.1 mL to 1 mL); 0.3=intestinal surface area ($cm^2$)]

Molecular biology techniques: ENaC (α, β and γ) mRNA expression, claudins 1, 2, 5, 7 and 8, occludin and E-cadherin), acid-sensing ion channels (ASIC1a) and aquaporins 1 and 5 by qRT-PCR.

Western blot analysis and immunohistochemistry: Western blot analysis and/or immunohistochemistry to determine protein levels and expression of ENaC (α, β and γ), tight junction proteins (claudins 1, 2, 5, 7 and 8, occludin and E-cadherin), acid-sensing ion channels (ASIC1a) and aquaporins 1 and 5.

EXAMPLES

Example 1

Methods: Mouse small intestines were used to study electrolyte absorption and intestinal barrier function (short-circuit current Isc, and conductance G), and net movement of chloride ($^{36}Cl$) and sodium ($^{22}Na$) was studied in Ussing chamber flux studies to quantitate the anion and cation absorptive capacity. AA-ORS were screened for their absorptive and secretory properties both in the presence and absence of cAMP secretagogue: forskolin (Fsk), which was used as a Cholera Toxin-like secretagogue. Separate mouse small intestinal loops were incubated in Ringers solution (RR) or each of the indicated exemplary AA-ORS to determine the absorptive and secretory nature of these formulations and brush border membrane vesicles (BBMV) were isolated from the small intestinal loops to determine the molecular identity of the transporters mediating such absorptive/secretory properties. Exemplary AA-ORS described herein were evaluated using a number of criteria, including, without limitation: sodium absorptive capacity, chloride secretory activity, effect on barrier function and the protein expression levels of the transporters or channels mediating sodium and chloride absorption.

Exemplary AA-ORS described herein exhibited enhanced electrolyte absorption. Combinations of free amino acids in each of the exemplary AA-ORS exhibited synergistic effect with respect to a variety of criteria, including net fluid absorption. See, for example, FIGS. 1-3. Exemplary AA-ORS formulations (e.g., F1, F4, F2, and F3) were tested in an anesthetized rat model for intestinal lumen perfusion in the presence of CT. Lumen perfusion studies showed that the F3 exhibited advantageous properties with respect to promoting net fluid absorption as reflected by a statistically significant increase of ~2.3 fold in net fluid absorption in the presence of CT when compared to that of WHO-ORS in the presence of CT. F1 and F2 also exhibited advantageous properties with respect to promoting net fluid absorption as reflected by statistically significant increases of ~2.0 fold in net fluid absorption in the presence of CT when compared to that of WHO-ORS in the presence of CT. See, for example, FIG. 2.

Lumen perfusion studies also showed that the F3 exhibited advantageous properties with respect to promoting net fluid absorption as reflected by a statistically significant increase of 56% in net fluid absorption in the presence of CT when compared to that of 8AA in the presence of CT. F1 also exhibited advantageous properties with respect to promoting net fluid absorption as reflected by a statistically significant increase of 42% in net fluid absorption in the presence of CT when compared to that of 8AA in the presence of CT. F2 also exhibited advantageous properties with respect to promoting net fluid absorption as reflected by a statistically significant increase of 31% in net fluid absorption in the presence of CT when compared to that of 8AA in the presence of CT. In contrast, F4, which contains 8 free amino acids (many of which are in common with F1, F2, and F3) conferred statistically significant lower net fluid absorption relative to 8AA. See FIG. 1.

Each of exemplary formulations F1, F2, and F3 comprise the following free amino acids: proline, aspartic acid, serine, arginine, tyrosine, threonine, and alanine. F2 and F3 comprise free amino acids of proline, aspartic acid, serine, arginine, tyrosine, threonine, alanine, and glycine. F1 comprises free amino acids of proline, aspartic acid, serine, arginine, tyrosine, threonine, alanine, and asparagine.

The results presented in FIGS. 1-3 demonstrate that factors such as the complement of free amino acids present in an amino acid formulation and the concentrations thereof contribute synergistically to the activity of amino acid formulations with respect to net fluid absorption conferred thereby.

Example 2

Studies may be performed to assess efficacy of amino acid formulations described herein. Such studies may include formulations that are considered standard of care for treating subjects afflicted with acute gastroenteritis. Acute gastroenteritis is a disease state that occurs when food or water that is contaminated with pathogenic microorganisms (such as *Clostridium perfringens, Vibrio cholera, E. coli*) or their toxins is consumed. Symptoms of acute gastroenteritis include at least one of nausea, vomiting, diarrhea, or abdominal pain, or any combination thereof. The WHO-ORS, which is a standard low-osmolarity glucose-based ORS, is an exemplary formulation for treating diarrhea that is routinely used in studies for treating diarrhea. Accordingly, the WHO-ORS may serve as a positive control in studies described herein.

Research Design and Methods

Design: Randomized, Double-Blind, Two-Cell Study

Study Population: The study subjects will be male children (to facilitate separate collection of urine and stool).

Inclusion criteria: Age: 6 months-36 months; Duration of diarrhea ≤48 hours; Some dehydration (judged clinically according to hospital accepted practice); Written informed consent by either parent/guardian.

Exclusion criteria: Severe malnutrition; Patients with diarrhea due to cholera; Systemic illness; Bloody diarrhea; Any congenital anomaly or disorder; Has documentation of taking antibiotic and/or antidiarrheal within the last 48 hours prior to hospitalization.

Study Procedures

Screening: All male children aged 6-36 months, presenting with diarrhea (onset ≤48 hours) and some dehydration will be screened by study nurses for possible inclusion in the study. All screened children will be kept in the hospital to perform a thorough clinical history and physical examination. Body weight and height will be measured and dehydration will be corrected according standard rehydration protocols.

Enrollment: Participants included in the study will be allocated into one of the ORS groups according to a predetermined randomization schedule. The enrolled children will then be randomized into groups, two groups of which will be treated with either an exemplary amino acid ORS described herein or WHO ORS.

Blinding Technique: The identity of specific product administered will be blinded to all persons involved in the study. Unblinding of product categories will occur only after statistical analysis has been performed.

Case management: The study patients will be placed on diarrhea cots. Initial treatment dosing with, e.g., WHO-ORS or an exemplary amino acid ORS described herein will be estimated using body weight in accordance with 5-10 ml/kg after each loose stool as per hospital guidelines, to maintain ongoing loss. Adjustments may be required, and hydration maintained using smaller or larger volumes depending on measured losses. Children will be fed using a spoon. Assessment and treatment will continue until resolution of diarrhea. Each participating child will be closely monitored for the occurrence of any adverse events such as worsening of diarrhea or increased vomiting, and their severity and duration will be noted and information recorded for analysis.

Laboratory Investigation

Routine: Blood will be obtained from a venipuncture to determine serum electrolytes and blood glucose will be determined on admission and 24 hours after enrollment. Complete blood count, serum creatinine, stool routine examination, bacterial culture and Rota viral antigen will also be performed for all patients on admission only. Other clinical laboratory investigations may be performed if clinically indicated.

Definitions

Duration of diarrhea in hospital: time in hours, from randomization till resolution of diarrhea.

Resolution of diarrhea: passage of the last liquid or semi-liquid stool prior to one soft/formed stools or no stool for 12 hours.

Stool output: The weight of stool in g/kg of admission body weight expressed per time period (i.e., per 24 hours and for the entire duration of diarrhea).

ORS and plain water intake: The total volume (in ml) of ORS or plain water taken in per kg of admission body weight, expressed per time period.

Sample Size Calculation and Outcome (Primary and Exploratory) Variable(s)

Sample size: Based on similar studies, a clinically significant improvement of 20% produces effect sizes of 0.4 to 0.7 (duration) and 0.3 (stool output) using the pooled standard deviations reported within each outcome.

Outcome Measures/Variables

Primary Outcome: Duration of diarrhea in hospital (hours)

Exploratory Outcomes: Stool output in the 1$^{st}$ 24 hours of hospitalization (g/kg body wt.), further divided into two 12-hour periods; Total stool output during hospitalization (g/kg body wt.); ORS intake in the 1$^{st}$ 24 hours of hospitalization (g/kg body wt.); Total ORS intake (ml/kg body wt.); Change in body weight (between pre-randomization and post-treatment); Urine output in the 1$^{st}$ 24 hours of hospitalization (g/kg body wt.); Total urine output during hospitalization (g/kg body wt.).

Differences between the treatment groups will be examined with respect to baseline characteristics prior to performing statistical analysis of the efficacy endpoints. If any differences are considered to be clinically important, subgroup analysis will be presented for the relevant endpoints.

Depending upon normality of distribution of the quantitative variables, t-test or Mann-Whitney U test will be used to compare the stool output, output of vomit, ORS intake, and/or duration of diarrhea. Comparison of the primary outcomes will be performed with and without adjustment of design effects (age stratum) and patient characteristics (cause, clinical characteristics on admission, nutritional status). All analyses will be performed separately on children as per-protocol and on all children in intention-to-treat basis.

The invention claimed is:

1. A formulation for use in treating diarrhea in a subject in need thereof, wherein the formulation comprises a therapeutically effective combination of free amino acids:

the free amino acids consisting essentially of a therapeutically effective amount of free amino acids of proline and aspartic acid; and a therapeutically effective amount of at least one of free amino acids of serine, threonine, glycine, alanine, arginine, or tyrosine, or any combination thereof; and optionally, free amino acids of asparagine; or optionally, monosaccharide glucose, at least one glucose-containing disaccharide, or any combination thereof, wherein the total concentration of the monosaccharide glucose, the at least one glucose-containing disaccharide, or any combination thereof is equal to or less than 90 mM; or optionally, at least one pharmaceutically acceptable carrier, buffer, electrolyte, adjuvant, excipient, or water, or any combination thereof; or any combination thereof; and wherein the therapeutically effective combination of free amino acids is sufficient to reduce at least one symptom associated with the diarrhea in the subject.

2. The formulation according to claim 1, wherein the concentration of proline ranges from 0.5 mM to 13 mM; wherein the concentration of aspartic acid ranges from 1 mM to 18 mM; wherein when serine is present, the concentration of serine ranges from 1.5 mM to 12 mM; wherein when threonine is present, the concentration of threonine ranges from 0.5 mM to 12 mM; wherein when glycine is present, the concentration of glycine ranges from 0.4 mM to 12 mM; wherein when alanine is present, the concentration of alanine ranges from 1.5 mM to 12 mM; wherein when arginine is present, the concentration of arginine ranges from 0.8 mM to 12 mM; wherein when tyrosine is present, the concentration of tyrosine ranges from 0.1 mM to 1.2 mM; wherein when asparagine is present, the concentration of asparagine ranges from 2 mM to 12 mM.

3. The formulation according to claim 1, wherein the therapeutically effective combination of free amino acids consists essentially of or consists of a therapeutically effective amount of free amino acids of proline, aspartic acid, serine, threonine, glycine, alanine, arginine, and tyrosine.

4. The formulation according to claim 1, wherein the therapeutically effective combination of free amino acids consists essentially of or consists of a therapeutically effective amount of free amino acids of proline, aspartic acid, serine, threonine, alanine, arginine, and tyrosine.

5. The formulation according to claim 1, wherein the formulation further comprises a pharmaceutically acceptable carrier, buffer, electrolyte, adjuvant, excipient, or water.

6. The formulation according to claim 1, wherein the formulation is sterile.

7. The formulation according to claim 1, wherein at least one of the free amino acids or each of the free amino acids comprises L-amino acids.

8. The formulation according to claim 1, wherein the formulation does not comprise monosaccharide glucose, at least one glucose-containing disaccharide, or any combination thereof.

9. The formulation according to claim 1, wherein the formulation is formulated for administration by a parenteral, pulmonary, inhalation, intranasal, enteral, intravenous, anal, or sublingual route.

10. The formulation according to claim 1, wherein the formulation is formulated for oral administration.

11. The formulation according to claim 1, wherein the subject is a mammal.

12. The formulation according to claim 11, wherein the mammal is a human, cat, dog, pig, horse, cow, sheep, or goat.

13. The formulation according to claim 11, wherein the mammal is a human.

14. The formulation according to claim 1, wherein the diarrhea is associated with an infection by bacteria that produce a secretagogue in the subject.

15. The formulation according to claim 14, wherein the bacteria comprise at least one of an enterotoxin-producing bacteria or an enterotoxigenic bacteria, or any combination thereof.

16. The formulation according to claim 15, wherein the enterotoxin-producing bacteria comprises *Vibrio cholerae, Staphylococcus aureus, Bacillus cereus, Clostridium difficile, Clostridium perfringens, Staphylococcus aureus, Yersinia enterocolitica, Shigella dysenteriae*, or an enterotoxigenic *Escherichia coli*, or any combination thereof.

17. The formulation according to claim 1, wherein the at least one symptom associated with diarrhea comprises at least one of loose, watery stools; abdominal cramps; abdominal pain; fever; blood in the stool; mucus in the stool; bloating; or nausea; or any combination thereof.

18. The formulation according to claim 1, wherein reducing the at least one symptom associated with diarrhea comprises a reduction in at least one of volume of loose, watery stools per day; or frequency of loose, watery stools per day; or any combination thereof.

19. The formulation according to claim 1, wherein the formulation is formulated for use as a medicament for the treatment of diarrhea.

20. A method for treating diarrhea in a subject in need thereof, the method comprising:

administering to the subject in need thereof the formulation according to claim 1, wherein the administering reduces at least one symptom associated with diarrhea in the subject.

* * * * *